US012569204B2

(12) United States Patent
Koehler et al.

(10) Patent No.: US 12,569,204 B2
(45) Date of Patent: Mar. 10, 2026

(54) METHOD AND SYSTEM FOR ANALYZING GLUCOSE MONITORING DATA INDICATIVE OF A GLUCOSE LEVEL

(71) Applicant: Roche Diabetes Care, Inc., Indianapolis, IN (US)

(72) Inventors: Matthias Koehler, Laudenbach (DE); Bernd Steiger, Roemerberg (DE); Timm Wiedemann, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

(21) Appl. No.: 17/826,273

(22) Filed: May 27, 2022

(65) Prior Publication Data

US 2022/0287654 A1 Sep. 15, 2022

Related U.S. Application Data

(63) Continuation of application No. 15/444,957, filed on Feb. 28, 2017, now Pat. No. 11,363,991.

(30) Foreign Application Priority Data

Mar. 2, 2016 (EP) .................................... 16158324

(51) Int. Cl.
*A61B 5/00* (2006.01)
*A61B 5/145* (2006.01)
*G16H 40/63* (2018.01)
(52) U.S. Cl.
CPC ........ *A61B 5/7275* (2013.01); *A61B 5/14532* (2013.01); *G16H 40/63* (2018.01)
(58) Field of Classification Search
CPC ... A61B 5/7275; A61B 5/14532; G16H 40/63
See application file for complete search history.

(56) References Cited

U.S. PATENT DOCUMENTS

2007/0033074 A1 2/2007 Nitzan et al.
2009/0150177 A1* 6/2009 Buck ....................... G16Z 99/00
                                              715/764
2010/0174553 A1 7/2010 Kaufman et al.
2011/0191343 A1* 8/2011 Heaton ................... G16Z 99/00
                                              707/E17.046
2013/0338453 A1 12/2013 Duke et al.

FOREIGN PATENT DOCUMENTS

WO WO 2012/084723 A1 6/2012
WO WO 2014/037365 A1 3/2014

OTHER PUBLICATIONS

Yaturu, Insulin therapies: Current and future trends at dawn, 2013, World J Diabetes, 4(1), p. 1-7 (Year: 2013).*
Rodbard, "Interpretation of Continuous Glucose Monitoring Data: Glycemic Variability and Quality of Glycemic Control," Diabetes Technology & Therapeutics, vol. 11, Supplement 1, Jun. 2, 2009, pp. S-55 to S-67, Mary Ann Liebert, Inc., New Rochelle, NY.
Disetronic Medical Systems Inc., "Accu-Chek Spirit Insulin Pump System Pump User Guide," 2008, 200 Pages.
Roche Diagnostics GMBH, "Accu-Check Smart Pix Device Reader User's Manual," Aug. 2010, 96 Pages.
Vashist, "Continuous Glucose Monitoring Systems: A Review," Diagnostics, Oct. 29, 2013, vol. 3, pp. 385 to 412, MDPI, Basel, CH.
Matthaei, "Assessing the value of the Ambulatory Glucose Profile in clinical practice," The British Journal of Diabetes and Vascular Disease, vol. 14, 2014, pp. 148 to 152.
Rodbard, "Continuous Glucose Monitoring: A Review of Successes, Challenges, and Opportunities," Diabetes Technology & Therapeutics, vol. 18, Supplement 2, 2016, pp. S2-3 to S2-13.
European Search Report, EP Application No. 16158324.0, Sep. 5, 2016, 12 pages.

* cited by examiner

*Primary Examiner* — Kaitlyn L Minchella
(74) *Attorney, Agent, or Firm* — Bose McKinney & Evans LLP

(57) ABSTRACT

A computer-implemented method and a system for analyzing glucose monitoring data indicative of a glucose level, comprising: presenting by a data processing device provided a graphical window on a display device wherein the graphical window comprises a time abscissa axis that defines time units, and a glucose ordinate axis that defines glucose units; receiving a plurality of glucose monitoring values associated with a monitoring time period by the data processing device; segmenting the plurality of glucose monitoring values into a plurality of glucose monitoring traces indicative of the glucose level; defining a reference trace segment; determining the reference trace segment for each of the plurality of glucose monitoring traces; and plotting, for a time window comprising the reference trace segment, the plurality of glucose monitoring traces within the graphical window. Furthermore, a non-transitory computer readable medium is disclosed.

11 Claims, 7 Drawing Sheets

METHOD AND SYSTEM FOR ANALYZING GLUCOSE MONITORING DATA INDICATIVE OF A GLUCOSE LEVEL

CROSS REFERENCE TO RELATED APPLICATIONS

This application is a continuation of U.S. application Ser. No. 15/444,957 filed on Feb. 28, 2017 entitled METHOD AND SYSTEM FOR ANALYZING GLUCOSE MONI- TORING DATA INDICATIVE OF A GLUCOSE LEVEL AND A NON-TRANSITORY COMPUTER READABLE MEDIUM which claims priority of EP application serial no. 16 158 324.0 filed on Mar. 2, 2016 entitled "Method and system for analyzing glucose monitoring data indicative of a glucose level, and a non-transitory computer readable medium" the disclosures of both of which are hereby incorporated herein by reference.

BACKGROUND

1. Technical Field

The present disclosure refers to a method and a system for analyzing glucose monitoring data indicative of a glucose level, and a non-transitory computer readable medium.

2. Description of the Related Art

Glucose monitoring helps people with diabetes manage the disease and avoid its associated problems. A person can use the results of glucose monitoring to make decisions about food, physical activity, and medications. A common way to check glucose level is performing discontinuous monitoring. Such checking usually involves pricking a fin- gertip with an automatic lancing device to obtain a blood sample and then using a glucose meter to measure the blood sample's glucose level. Such monitoring may also be referred to as spot monitoring.

As an alternative, or, in addition, continuous glucose monitoring (CGM) may be applied. A system for CGM may use a body sensor inserted under the skin to check glucose levels. The sensor stays in place for several days to weeks and then must be replaced. A transmitter sends information about an analyte value or level indicative of the glucose level (e.g., via wireless data transmission) from the sensor to a monitor device. The user may check blood samples with a glucose meter to calibrate the devices.

Patients with diabetes may be asked to perform a number of collections in an effort to diagnose a chronic DC or to optimize therapy. For example, diabetic patients may measure their glucose level concurrently with various events that occur according to the patient's lifestyle. The events may or may not be correlated with or influence biomarkers of the chronic DC or the optimization or therapy. However, the correlations between the events in the biomarkers of the chronic DC can be difficult to identify. Methods and systems were proposed for visualizing correlations between glucose data and events.

Document US 2007/0033074 A1 discloses a diabetes data management system selecting variable parameters and one or more devices with data that are utilized in a report. The diabetes data management system analyses data during a selected period. The system generates reports which high- light data from one or more device during the selected period including carbohydrate, insulin, and glucose data, reports which highlight data around and during meal events and other user-defined events, reports which overlay multiple data based on time of day and other factors, and automati- cally prepared logbook reports.

Document US 2010/0174553 A1 refers to a method of diabetes analysis. A plurality of glucose level readings for a user is received. The plurality of blood glucose level read- ings is analyzed to generate a report. The report includes a first chart along a 24-hour timeline indicating the plurality of glucose level readings, and a second chart having at least one of infusion device settings and active insulin levels corresponding to the 24-hour timeline of the first chart.

Document WO 2014/037365 A1 refers to methods and apparatuses for visualizing correlations between blood glu- cose data and events. The methods and apparatus can include presenting an event analysis window on a display communicatively coupled to one or more processors. The event analysis window can include an event type control positioned with the event analysis window and a graphical window positioned within the event analysis window. A plurality of continuous glucose monitoring traces can be plotted within the graphical window. Bolus icons each indicative of a bolus amount and a bolus time can be presented within the event analysis window. Each of the bolus icons can include a bolus indication object that is aligned with the bolus ordinate axis within the graphical window, a bolus time indication object that is aligned with the time abscissa axis within in the graphical window, and a bolus symbol that is presented outside of the graphical window. An event selection input can be received by the one or more processors. For example, a meal comparison can be received as the event selection input. The meal comparison can be associated with a plurality of event instances such as, for example, at least a portion of a collected data or any data that is associated with biomarker data. Each of the event instances can be associated with an event time, i.e. the event instances can be indexed such that the event instances can be demarcated according to time. A reference time can be defined. The reference time generally corresponds to a normalized point in time that is indicative of the occurrence of an event. Accordingly, events can be presented visually in alignment with one another along a time access of graphical window for plotting a plurality of glucose traces.

SUMMARY

It is an object of the present disclosure to provide improved technology for analyzing glucose monitoring data indicative of a glucose level in a bodily fluid.

A method and a system are disclosed for analyzing glucose monitoring data indicative of a glucose level in a bodily fluid. Further, a computer program product is described. Alternative embodiments are also disclosed.

According to an aspect of the disclosure, a computer- implemented method for analyzing glucose monitoring data indicative of a glucose level is provided. A graphical win- dow is presented by a data processing device provided with one or more processors on a display device communica- tively coupled to the data processing device, wherein the graphical window comprises a time abscissa axis that defines time units, and a glucose ordinate axis that defines glucose units. A plurality of glucose monitoring values associated with a monitoring time period is received by the data processing device, the plurality of glucose monitoring values indicating a glucose level sampled for a person in a bodily fluid in a glucose level measurement. The plurality of glucose monitoring values is segmented by the data processing device into a plurality of glucose monitoring traces indicative of the glucose level, wherein each of the plurality of glucose monitoring traces spans a measurement time segment of the monitoring time period. A reference trace segment is defined by the data processing device. The reference trace segment is determined by the data processing device for each of the plurality of glucose monitoring traces. The plurality of glucose monitoring traces is plotted for a time window comprising the reference trace segment within the graphical window, wherein the plurality of glucose monitoring traces are scaled according to the time abscissa axis and the glucose ordinate axis, and the plurality of glucose monitoring traces are aligned with regard to the reference trace segment.

According to another aspect of the disclosure, a system comprising a data processing device provided with one or more processors and a display device communicatively coupled to the data processing device is provided. The system is configured to: present by the data processing device a graphical window on a display device communicatively coupled to the data processing device, wherein the graphical window comprises a time abscissa axis that defines time units, and a glucose ordinate axis that defines glucose units; receive a plurality of glucose monitoring values associated with a monitoring time period by the data processing device, the plurality of glucose monitoring values indicating a glucose level sampled for a person in a bodily fluid in a glucose level measurement; segment by the data processing device the plurality of glucose monitoring values into a plurality of glucose monitoring traces indicative of the glucose level, wherein each of the plurality of glucose monitoring traces spans a measurement time segment of the monitoring time period; define by the data processing device a reference trace segment; determine by the data processing device the reference trace segment for each of the plurality of glucose monitoring traces; and plot, for a time window comprising the reference trace segment, the plurality of glucose monitoring traces within the graphical window, wherein the plurality of glucose monitoring traces are scaled according to the time abscissa axis and the glucose ordinate axis, and the plurality of glucose monitoring traces are aligned with regard to the reference trace segment.

Further, a non-transitory computer readable medium is provided.

The glucose monitoring data is a stream of data collected or sampled for a bodily fluid of a person or patient for a plurality of sample times over the measurement or monitoring time period in a glucose level monitoring. The sample time is a parameter that indicates when, during the measurement or monitoring time period, the respective glucose value is detected in the glucose level measurement. The term sample time as referred to here may define a fixed time. In an alternative embodiment, for glucose values from different glucose profiles all assigned to the "same sample time" the actual sample times may be spread over a short period of time, e.g. one or several minutes or even an hour. In such case, the sample time for which the glucose values from the different glucose profiles are compared is not a single defined time. Rather, the sample time is a (limited) period of time. For example, such sample time spreading may take place if the glucose monitoring is done on different days.

In an embodiment, a glucose monitoring trace which may also be referred to as glucose profile comprises a glucose value for each of the plurality of sample times over the measurement time segment. Such measurement time segment, for example, may be 24 h.

The time window for which the plurality of glucose monitoring traces are plotted within the graphical window may extend over the measurement time segment of one of the plurality of glucose monitoring traces as whole or in part.

The reference trace segment may be a single point or a group of points along the glucose monitoring trace for which it is determined.

The reference trace segment may be determined for each of the plurality of glucose monitoring traces exclusively based on a definition of trace characteristic(s) which may also be referred to as curve or profile characteristic(s). Specifically, determining the reference trace segment for each of the plurality of glucose monitoring traces is performed free of reference to time definition with regard to the time abscissa axis and/or the sample time. The reference trace segment may be determined in the glucose monitoring traces by a graph analysis conducting a search for the reference trace segment along the course of the respective glucose monitoring trace. Such analysis may be referred to as a time indexed free trace analysis, the reference trace segment not being time indexed in the process of trace analysis.

The plurality of glucose monitoring values associated with the monitoring time period may be received from a data storage medium storing the plurality of glucose monitoring values prior to the transmission to the data processing device. The analyzing of the glucose monitoring values may be performed retrospectively after the monitoring time period has ended.

The method may further comprise defining, by the data processing device, a reference time along the time abscissa axis; and normalizing the reference trace segment for each of the plurality of glucose monitoring traces to the reference time. The reference time is provided as a normalized point or range in time. With regard to the time abscissa axis, the aligning leads to total overlapping or overlapping in part of the reference trace segment for each of the plurality of glucose monitoring traces. Thereby, after the reference trace segment has been determined by the trace, profile or curve analysis, for plotting the plurality of glucose monitoring traces presented within the graphical window may be normalized to the reference time (normalized time segment) along the time abscissa axis.

The method may further comprise defining, by the data processing device, a reference glucose value along the glucose ordinate axis to the reference trace segment for each of the plurality of glucose monitoring traces; and normalizing the plurality of glucose monitoring traces to the reference glucose value. The reference glucose value is provided as a normalized point or range in terms of glucose values. With regard to the glucose ordinate axis, the aligning leads to total overlapping or overlapping in part of the reference glucose value assigned to the reference trace segment for each of the plurality of glucose monitoring traces. Thereby, the plurality of glucose monitoring traces presented within the graphical window may be normalized to the reference glucose value (normalized glucose value segment) along the glucose ordinate axis.

The defining may comprise selecting, by the data processing device, the reference trace segment from the following group: a local minimum trace segment indicating a local minimum glucose value segment; a local maximum trace segment indicating a local maximum glucose value segment; an absolute minimum trace segment indicating an absolute minimum glucose value segment; an absolute minimum trace segment indicating an absolute minimum glucose value segment; and an inflection trace point.

The receiving may comprise receiving, by data processing device, a plurality of continuous glucose monitoring values associated with the monitoring time period, the plurality of continuous glucose monitoring values indicating a glucose level sampled for the person in the bodily fluid in a continuous glucose level measurement.

The receiving may comprise receiving, by data processing device receiving, a plurality of discontinuous glucose monitoring values associated with the monitoring time period, the plurality of discontinuous glucose monitoring values indicating a glucose level sampled for the person in the bodily fluid in a discontinuous glucose level measurement. The discontinuous glucose level measurement may be a spot monitoring, e.g. a blood glucose spot monitoring.

The defining may comprise, by data processing device, providing a trace range selection, the trace range selection defining a trace range for the plurality of glucose monitoring traces; and determining the reference trace segment within the trace range selection for each of the plurality of glucose monitoring traces. The trace range selection is limiting the segments or parts of the glucose monitoring traces for which the reference trace segment may be determined. If a trace range selection is provided in the data processing device, the reference trace segment may not be determined from trace segments lying outside the trace range selection. For example, a local minimum or maximum may be determined within the trace range selection. The trace range selection is limiting the segments or parts in the glucose monitoring traces for which the reference trace segment may be determined, e.g., to a defined time range (e.g. day, day of the week, daytime, nighttime, breakfast time, lunch time, dinner time, snack time, bedtime).

The defining may comprise determining by the data processing device the trace range selection from a selection parameter received by the data processing device.

The selection parameter may be selected from the following group: day; day of the week; and daytime etc. In response to the selection parameter, for the plurality of glucose monitoring traces, limited segments or parts of the trace are determined which are analyzed for determining the reference trace segment. Within the limited segments, the reference trace segment is determined, the determining disregarding sample time information assigned to the limited segment of the trace. For example, a lunch time period from 1 p.m. to 2 p.m. may be provided as the selection parameter. In response, the segment of the traces assigned to such time limit is selected for determining the reference trace segment. For example, the reference trace segment may be determined to be a local minimum or a local maximum of the trace within such time limit.

The defining may comprise defining, by the data processing device, the reference trace segment in response to receiving a user input by the data processing device through an input device communicatively coupled to the data processing device. The user input may indicate a selection parameter. As an alternative, through the input device the user may select a segment of the glucose monitoring traces plotted within a graphical window on the display device, thereby, defining the trace range selection. For example, the user may select a segment of the trace by means of a mouse device or through a touch sensitive display. Following, the reference trace segment selected by the user is determined within such trace range selection by the data processing device.

For at least two of the plurality of glucose monitoring traces the reference trace segment may be assigned to a different sample time. In addition, for the at least two of the plurality of glucose monitoring traces the reference trace segment may be assigned to a different daytime.

The glucose monitoring data may be analyte monitoring data providing a stream of data collected or sampled for a person or patient for a plurality of sample times over a measurement time period in an analyte level monitoring, the analyte level being indicative of a glucose level in a bodily fluid.

With regard to a glucose measurement or monitoring, a glucose level or value may be determined by analyzing a blood sample via e.g. spot monitoring, and, as an alternative or in addition, by continuous glucose monitoring (CGM) via a fully or partially implanted sensor. In general, in the context of CGM a glucose value or level in a bodily fluid may be determined. The analyte value may be, e.g., subcutaneously measured in an interstitial fluid. CGM may be implemented as a nearly real-time or quasi-continuous monitoring procedure frequently or automatically providing/updating analyte values without user interaction.

The various embodiments referred to above with regard to a method may also apply to the system.

BRIEF DESCRIPTION OF THE DRAWINGS

The above mentioned and other features of this invention, and the manner of attaining them, will become more apparent and the invention itself will be better understood by reference to the following description of embodiments of the invention taken in conjunction with the accompanying drawings, wherein.

Figure 1:
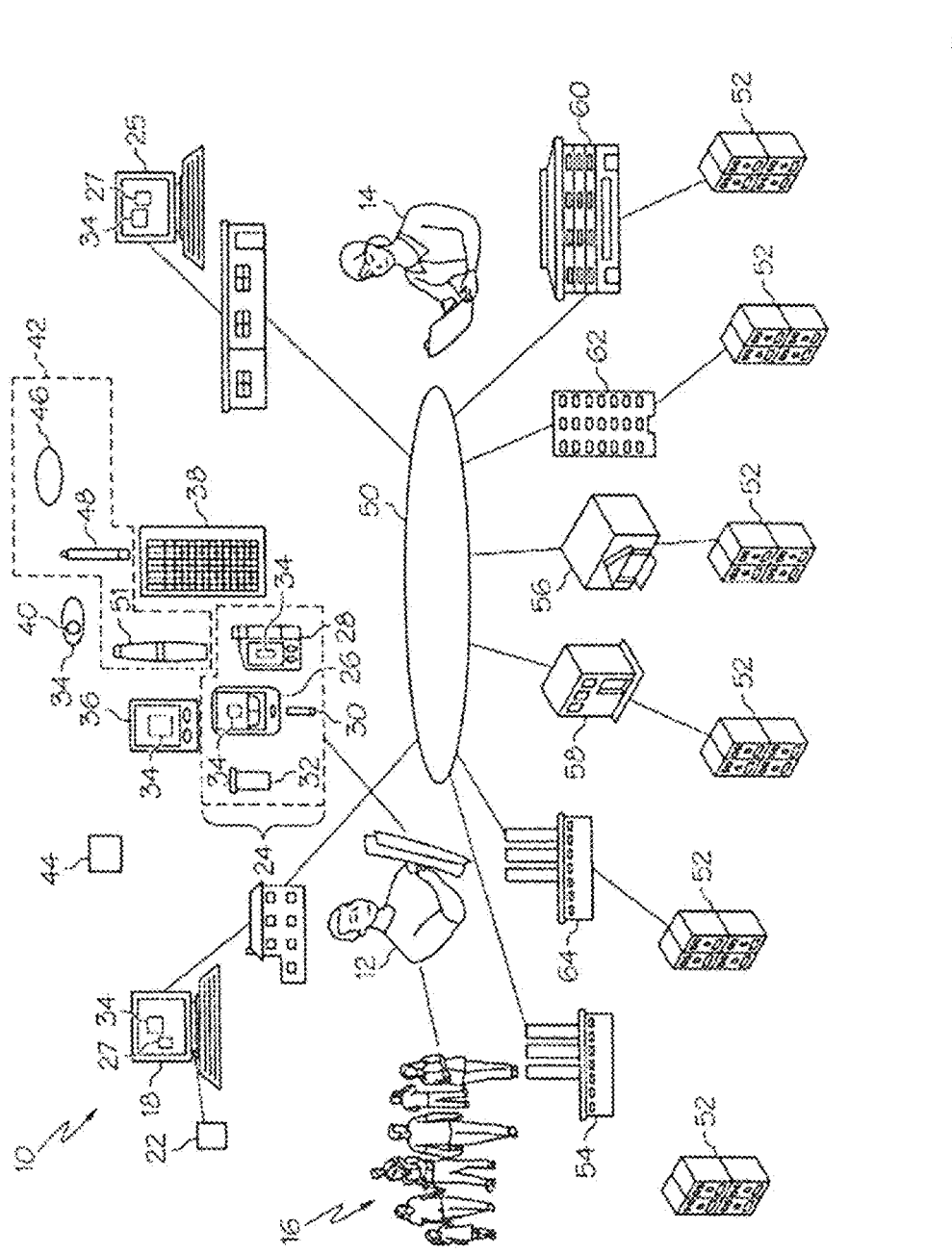
FIG. 1 is a schematic representation of a chronic care management system for a diabetes patient.

Corresponding reference characters indicate corresponding parts throughout the several views. Although the exemplification set out herein illustrates embodiments of the invention, in several forms, the embodiments disclosed below are not intended to be exhaustive or to be construed as limiting the scope of the invention to the precise forms disclosed.

DETAILED DESCRIPTION

FIG. 1 shows a chronic care management system 10 for a diabetes patient(s) 12 and a clinician(s) 14 along with others 16 having an interest in the chronic care management of the patient 12. Patient 12, having dysglycemia, may include persons with a metabolic syndrome, pre-diabetes, type 1 diabetes, type 2 diabetes, and gestational diabetes. The others 16 with an interest in the patient's care may include family members, friends, support groups, and religious organizations all of which can influence the patient's conformance with therapy. The patient 12 may have access to a patient computer 18, such as a home computer, which can connect to a public network 50 (wired or wireless), such as the internet, cellular network, etc., and couple to a dongle, docking station, or device reader 22 for communicating with an external portable device, such as a portable collection device 24 (see FIG. 2). An example of a device reader is shown in the manual "Accu-Chek® Smart Pix Device Reader User's Manual" (2008) available from Roche Diagnostics.

The collection device 24 can be essentially any portable electronic device that can function as an acquisition mechanism for determining and storing digital glucose value(s), such as a continuous or a discontinuous glucose monitoring.

In one embodiment, the collection device 24 can be a self-monitoring blood glucose meter 26 or a continuous glucose monitor 28.

In addition to the collection device 24, the patient 12 can use a variety of products to manage his or her diabetes including: test strips 30 carried in a vial 32 for use in the collection device 24; software 34 which can operate on the patient computer 18, the collection device 24, a handheld computing device 36, such as a laptop computer, a personal digital assistant, and/or a mobile phone; and paper tools 38. Software 34 can be pre-loaded or provided either via a computer readable medium 40 or over the public network 50 and loaded for operation on the patient computer 18, the collection device 24, the clinician computer/office workstation 25, and the handheld computing device 36, if desired. In still other embodiments, the software 34 can also be integrated into the device reader 22 that is coupled to the computer (e.g., computers 18 or 25) for operation thereon, or accessed remotely through the public network 50, such as from a server 52.

The patient 12 can also use, for certain diabetes therapies, additional therapy devices 42 and other devices 44. Therapy devices 42 can include devices such as an ambulatory infusion pump 46, an insulin pen 48, and a lancing device 51. An example of an ambulatory insulin pump 46 include but not limited thereto the Accu-Chek® Spirit pump described in the manual "Accu-Chek® Spirit Insulin Pump System Pump User Guide" (2007) available from Roche Diabetes Care. The other devices 44 can be medical devices that provide patient data such as blood pressure, fitness devices that provide patient data such as exercise information, and elder care device that provide notification to care givers. The other devices 44 can be configured to communicate with each other according to standards planned by Continua® Health Alliance.

The clinicians 14 for diabetes are diverse and can include, for example, nurses, nurse practitioners, physicians, endocrinologists, and other such health care providers. The clinician 14 typically has access to a clinician computer 25, such as a clinician office computer, which can also be pro-vided with the software 34. A healthcare record system 27, such as Microsoft® Health Vault™ and Google™ Health, may also be used by the patient 12 and the clinician 14 on computers 18, 25 to exchange information via the public network 50 or via other network means (LANs, WANs, VPNs, etc.), and to store information such as collection data from the collection device 24 to an electronic medical record of the patient e.g., EMR which can be provided to and from computer 18, 25 and/or server 52.

Figure 2:
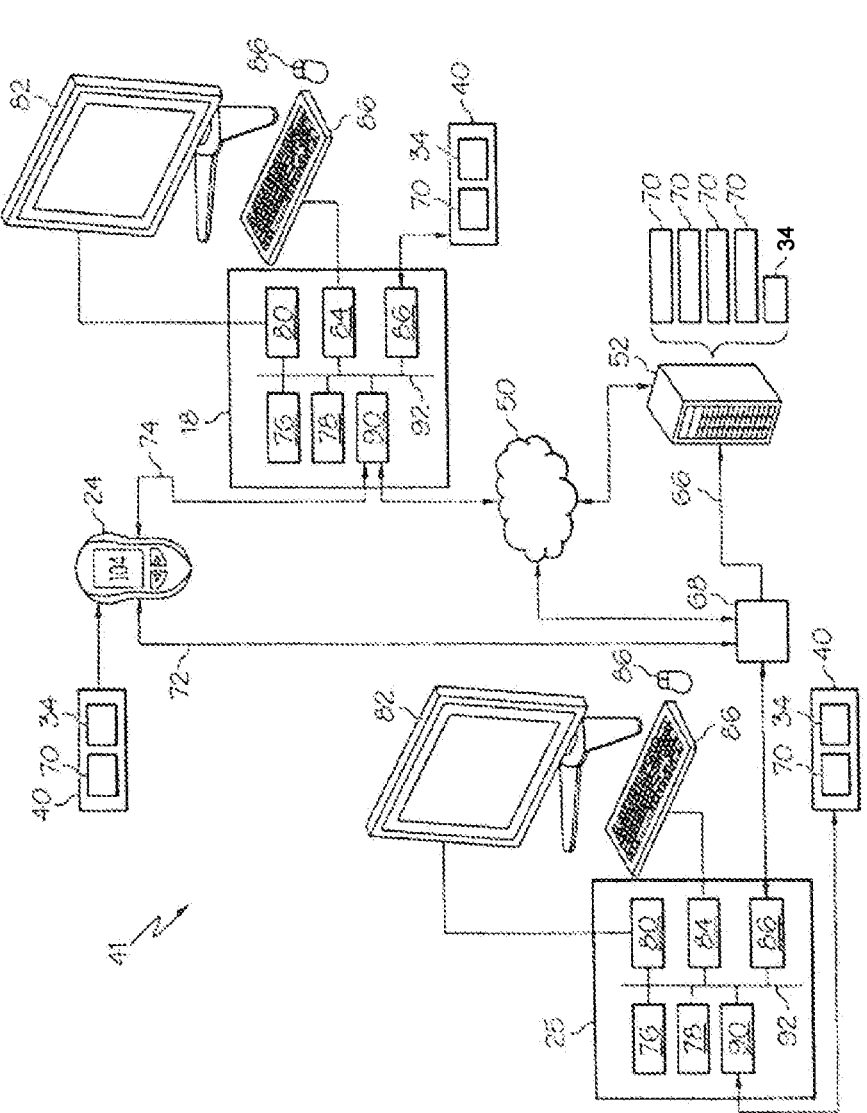
FIG. 2 is a schematic representation of a system suitable for implementing a computer-implemented method or graphical user interface.

Most patients 12 and clinicians 14 can interact over the public network 50 with each other and with others having computers/servers 52. Such others can include the patient's employer 54, a third party payer 56, such as an insurance company who pays some or all of the patient's healthcare expenses, a pharmacy 58 that dispenses certain diabetic consumable items, a hospital 60, a government agency 62, which can also be a payer, and companies 64 providing healthcare products and services for detection, prevention, diagnosis and treatment of diseases. The patient 12 can also grant permissions to access the patient's electronic health record to others, such as the employer 54, the payer 56, the pharmacy 58, the hospital 60, and the government agencies 62 via the healthcare record system 27, which can reside on the clinician computer 25 and/or one or more servers 52. Reference hereafter is also made to FIG. 2.

FIG. 2 shows a system 41 suitable for implementing embodiments of the technologies described herein, which in another embodiment can be a part of the chronic care management system 10 and communicate with such components, via conventional wired or wireless communication means. As an alternative, only selected elements of the system 41 may be provided for implementing the technologies described herein. For example, analyzing and visualizing of the glucose values may be done in the collection device 24 and/or some of the data processing devices (computer) communicatively connected to the collection device 24.

The system 41 can include the clinician computer 25 that is in communication with a server 52 as well as the collection device 24. Communications between the clinician computer 25 and the server 52 can be facilitated via a communication link to the public network 50, to a private network 66, or combinations thereof. The private network 66 can be a local area network or a wide area network (wired or wireless) connecting to the public network 50 via a network device 68 such as a (web) server, router, modem, hub, and the like.

In one embodiment, the server 52, as well as the network device 68, can function also as a data aggregator for collected glucose monitoring data 70. Accordingly, in such an embodiment, the glucose monitoring data 70 of a completed collection procedure(s) from a collection device of the patient 12 can then be provided from the server 52 and/or network device 68 to the clinician computer 25 when requested in response to a retrieval for such patient data.

In one embodiment, one or more of a plurality of instances of glucose monitoring data 70 aggregated on the server 52 can be provided over the public network 50, such as through a secure web interface implemented on the patient computer 18, the clinician computer 25, and/or the collection device 24. In another embodiment, the clinician computer 25 can serve as the interface (wired or wireless) 72 between the server 52 and the collection device 24. In still another embodiment, glucose monitoring data 70, as well as software 34, may be provided on a computer readable medium 40 and loaded directly on the patient computer 18, the clinician computer 25, and/or the collection device 24. In still another embodiment, glucose monitoring data 70 and software 34 may be sent between the patient computer 18, the clinician computer 25, the server 52 and/or the collection device 24 via the public network 50, the private network 66, via a direct device connection (wired or wireless) 74, or combinations thereof. Accordingly, in one embodiment the external devices e.g., computer 18 and 25, can be used to establish a communication link 72, 74 between the collection device 24 and still further electronic devices such as other remote Personal Computer (PC), and/or servers such as through the public network 50, such as the Internet and/or other communication networks (e.g., LANs, WANs, VPNs, etc.), such as private network 66.

The patient computer 18, as a conventional personal computer/workstation, can include a processor 76 which executes programs, such as software 34, and such as from memory 78 and/or computer readable medium 40. Memory 78 can include system memory (RAM, ROM, EEPROM, etc.), and storage memory, such as hard drives and/or flash memory (internal or external). The patient computer 18 can also include a graphics processor 80 (e.g., to interface a display 82 with the processor 76, input/output connections 84 for connecting user interface devices 86, such as a keyboard and mouse (wired or wireless), and computer readable drives 88 for portable memory and discs, such as computer readable medium 40. The patient computer 18 can further include communication interfaces 90 for connections to the public network 50 and other devices, such as collection device 24 (wired or wireless), and a bus interface 92 for connecting the above mentioned electronic components to the processor 76.

Figure 3:
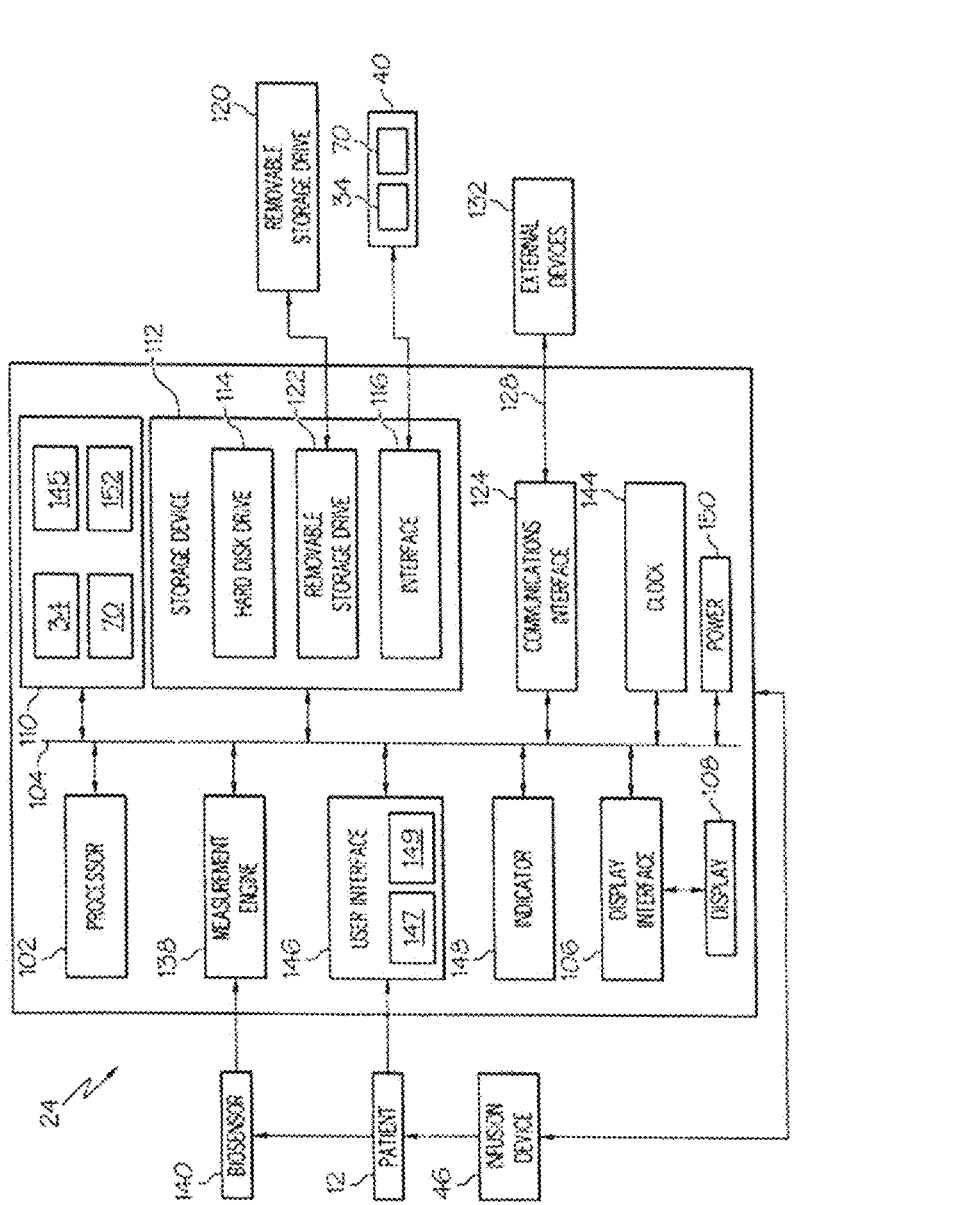
FIG. 3 is a schematic representation of a collection device for collecting glucose monitoring data.

Similarly, the clinician computer 25, as a conventional personal computer/workstation, can include a processor 76 which executes programs, such as software 34, and such as from memory 78 and/or computer readable medium 40. The clinician computer 25 can also include a graphics processor 80 to interface a display 82 with the processor 76, input/output connections 84 for connecting user interface devices 86, such as a keyboard and mouse (wired or wireless), and computer readable drives 88 for portable memory and discs, such as computer readable medium 40. The clinician computer 25 can further include communication interfaces 90 for connections to the public network 50 and other devices, such as collection device 24 (wired or wireless), and a bus interface 92 for connecting the above mentioned electronic components to the processor 76. Reference hereafter is now made to FIG. 3.

FIG. 3 is a block diagram conceptually illustrating the portable collection device 24 depicted in FIG. 2. In the illustrated embodiment, the collection device 24 can include one or more microprocessors, such as processor 102, which maybe a central processing unit comprising at least one more single or multicore and cache memory, which can be connected to a bus 104, which may include data, memory, control and/or address buses. The collection device 24 can include the software 34, which provides instruction codes that causes a processor 102 of the device to implement the methods provided herein. The collection device 24 may include a display interface 106 providing graphics, text, and other data from the bus 104 (or from a frame buffer not shown) for display on a display 108. The display interface 106 may be a display driver of an integrated graphics solution that utilizes a portion of main memory 110 of the collection device 24, such as random access memory (RAM) and processing from the processor 102 or may be a dedicated graphic processing unit. In another embodiment, the display interface 106 and display 108 can additionally provide a touch screen interface for providing data to the collection device 24 in a well-known manner.

Main memory 110 in one embodiment can be random access memory (RAM), and in other embodiments may include other memory such as a ROM, PROM, EPROM or EEPROM, and combinations thereof. In one embodiment, the collection device 24 can include secondary memory 112, which may include, for example, a hard disk drive 114 and/or a computer readable medium drive 116 for the computer readable medium 40, representing for example, at least one of a floppy disk drive, a magnetic tape drive, an optical disk drive, a flash memory connector (e.g., USB connector, Firewire connector, PC card slot), etc. The drive 116 reads from and/or writes to the computer readable medium 40 in a well-known manner. Computer readable medium 40, represents a floppy disk, magnetic tape, optical disk (CD or DVD), flash drive, PC card, etc. which is read by and written to by the drive 116. As will be appreciated, the computer readable medium 40 can have stored therein the software 34 and/or glucose monitoring data 70 resulting from completed collections performed according to one or more of the collection procedures.

In alternative embodiments, secondary memory 112 may include other means for allowing the software 34, other computer programs or other instructions to be loaded into the collection device 24. Such means may include, for example, a removable storage unit 120 and an interface connector 122. Examples of such removable storage units/interfaces can include a program cartridge and cartridge interface, a removable memory chip (e.g., ROM, PROM, EPROM, EEPROM, etc.) and associated socket, and other removable storage units 120 (e.g. hard drives) and interface connector 122 which allow software and data to be transferred from the removable storage unit 120 to the collection device 24.

The collection device 24 in one embodiment can include a communication module 124. The communication module 124 allows software and data (e.g., glucose monitoring data 70 resulting from completed collections) to be transferred between the collection device 24 and an external device(s) 126. Examples of communication module 124 may include one or more of a modem, a network interface (such as an Ethernet card), a communications port (e.g., USB, Firewire, serial, parallel, etc.), a PC or PCMCIA slot and card, a wireless transceiver, and combinations thereof. The external device 126 can be the patient computer 18, the clinician computer 25, the handheld computing devices 36, such as a laptop computer, a personal digital assistance (PDA), a mobile (cellular) phone, and/or a dongle, a docking station, or device reader 22. In such an embodiment, the external device 126 may provide and/or connect to one or more of a modem, a network interface (such as an Ethernet card), a communications port (e.g., USB, Firewire, serial, parallel, etc.), a PCMCIA slot and card, a wireless transceiver, and combinations thereof for providing communication over the public network 50 or private network, such as with the clinician computer 25 or server 52. Software and data transferred via communication module 124 can be in the form of wired or wireless signals 128, which may be electronic, electromagnetic, optical, or other signals capable of being sent and received by communication module 124. For example, as is known, signals 128 maybe sent between communication module 124 and the external device(s) 126 using wire or cable, fiber optics, a phone line, a cellular phone link, an RF link, an infrared link, other communications channels, and combinations thereof. Specific techniques for connecting electronic devices through wired and/or wireless connections (e.g. USB and Bluetooth, respectively) are well known in the art.

In another embodiment, the collection device 24 can be used with the external device 132, such as provided as a handheld computer or a mobile phone, to perform actions such as prompt a patient to take an action, acquire a data event, and perform calculations on information.

In the illustrative embodiment, the collection device 24 can provide a measurement engine 138 for reading a biosensor 140. The biosensor 140, which in one embodiment is the disposable test strip 30 (FIG. 1), is used with the collection device 24 to receive a sample such as for example, of capillary blood, which is exposed to an enzymatic reaction and measured by electrochemistry techniques, optical techniques, or both by the measurement engine 138 to measure and provide a glucose monitoring value, such as for example, a blood glucose level. In other embodiments, the measurement engine 138 and biosensor 140 can be of a type used to provide a glucose monitoring value for other types of sampled fluids or analytes besides or in addition to glucose, heart rate, blood pressure measurement, and combinations thereof. Such an alternative embodiment is useful in embodiments where values from more than one glucose monitoring type are requested by a structured collection procedure. In still another embodiment, the biosensor 140 may be a sensor with an indwelling catheter(s) or being a subcutaneous tissue fluid sampling device(s), such as when the collection device 24 is implemented as a continuous glucose monitor (CGM), optionally in communication with an infusion device, such as insulin pump 46 (FIG. 1). In alternative embodiments, the collection device 24 can be a controller implementing the software 34 and communicating between the infusion device (e.g., ambulatory insulin pump 46 and electronic insulin pen 48) and the biosensor 140.

Data, comprising at least the information collected by the biosensor 140, is provided by the measurement engine 138 to the processor 102 which may execute a computer program 152 stored in memory 110 to perform various calculations and processes using the data. The data from the measurement engine 138 and the results of the calculation and processes by the processor 102 using the data is herein referred to as self-monitored data. The self-monitored data may include, but not limited thereto, the glucose values of a patient 12, the insulin dose values, the insulin types, and the parameter values used by processor 102 to calculate future glucose values, supplemental insulin doses, and carbohydrate supplement amounts as well as such values, doses, and amounts. Such data along with a date-time stamp for, e.g., each measured glucose value and optionally each administered insulin dose value is stored in a data file 145 of memory 110 and/or 112. An internal clock 144 of the collection device 24 can supply the current date and time to processor 102 for such use.

The collection device 24 can further provide a user interface 146, such as buttons, keys, a trackball, touchpad, touch screen, etc. for data entry, program control and navigation of selections, choices and data, making information requests, and the like. In one embodiment, the user interface 146 can comprises one or more buttons 147, 149 for entry and navigation of the data provided in memory 110 and/or 112. In one embodiment, the user can use one or more of buttons 147, 149 to enter (document) contextualizing information, such as data related to the everyday lifestyle of the patient 12 and to acknowledge that prescribed tasks are completed. Such lifestyle data may relate to food intake, medication use, energy levels, exercise, sleep, general health conditions and overall well-being sense of the patient 12 (e.g., happy, sad, rested, stressed, tired, etc.). Such lifestyle data can be recorded into memory 110 and/or 112 of the collection device 24 as part of the self-monitored data via navigating through a selection menu displayed on display 108 using buttons 147, 149 and/or via a touch screen user interface provided by the display 108. It is to be appreciated that the user interface 146 can also be used to display on the display 108 the self-monitored data or portions thereof, such as used by the processor 102 to display measured glucose levels as well as any entered data.

In one embodiment, the collection device 24 can be switched on by pressing any one of the buttons 147, 149 or any combination thereof. In another embodiment, in which the biosensor 140 is a test-strip, the collection device 24 can be automatically switched on when the test-strip is inserted into the collection device 24 for measurement by the measurement engine 138 of a glucose level in a sample of blood placed on the test-strip. In one embodiment, the collection device 24 can be switched off by holding down one of the buttons 147, 149 for a pre-defined period of time, or in another embodiment can be shut down automatically after a pre-defined period of non-use of the user interface 146.

An indicator 148 can also be connected to processor 102, and which can operate under the control of processor 102 to emit audible, tactile (vibrations), and/or visual alerts/reminders to the patient of daily times for BG measurements and events, such as for example, to take a meal, of possible future hypoglycemia, and the like. A suitable power supply 150 is also provided to power the collection device 24 as is well known to make the device portable.

As mentioned above previously, the collection device 24 may be pre-loaded with the software 34 or be provided therewith via the computer readable medium 40 as well as received via the communication module 124 by signal 128 directly or indirectly though the external device 132 and/or network 50. When provided in the latter matter, the software 34 when received by the processor 102 of the collection device 24 is stored in main memory 110 (as illustrated) and/or secondary memory 112. The software 34 contains instructions, when executed by the processor 102, enables the processor to perform the features/functions as discussed herein. In another embodiment, the software 34 may be stored in the computer readable medium 40 and loaded by the processor 102 into cache memory to cause the processor 102 to perform the features/functions as described herein. In another embodiment, the software 34 is implemented primarily in hardware logic using, for example, hardware components such as application specific integrated circuits (ASICs). Implementation of the hardware state machine to perform the feature/functions described herein will be apparent to persons skilled in the relevant art(s). In yet another embodiment, the technology is implemented using a combination of both hardware and software.

It is to be appreciated that glucose monitoring data 70, which can include or be associated with self-monitored data and/or contextual information can be sent/downloaded (wired or wireless) from the collection device 24 via the communication module 124 to another electronic device, such as the external device 132 (PC, PDA, or cellular telephone), or via the network 50 to the clinician computer 25. Clinicians can use diabetes software provided on the clinician computer 25 to evaluate the received glucose monitoring data 70 of the patient 12 for therapy results.

In one embodiment, the collection device 24 can be provided as portable blood glucose meter, which is used by the patient 12 for recording self-monitored data comprising insulin dosage readings and spot measured glucose levels. Accordingly, it is to be appreciated that the collection device 24 can include the software and hardware necessary to process, analyze and interpret the self-monitored data in accordance with predefined flow sequences (as described below in detail) and generate an appropriate data interpretation output. In one embodiment, the results of the data analysis and interpretation performed upon the stored patient data by the collection device 24 can be displayed in the form of a report, trend-monitoring graphs, and charts to help patients manage their physiological condition and support patient-doctor communications. In other embodiments, the BG data from the collection device 24 may be used to generate reports (hardcopy or electronic) via the external device 132 and/or the patient computer 18 and/or the clinician computer 25.

The collection device 24 can further provide the user and/or his or her clinician with at least one or more of the possibilities comprising: a) editing data descriptions, e. g. the title and description of a record; b) saving records at a specified location, in particular in user-definable directories as described above; c) recalling records for display; d) searching records according to different criteria (date, time, title, description etc.); e) sorting records according to different criteria (e.g., values of the BG level, date, time, duration, title, description, etc.); f) deleting records; g) exporting records; and/or h) performing data comparisons, modifying records, excluding records as is well known.

In still another embodiment, the software 34 can be implemented on the continuous glucose monitor 28 (FIG. 1). In this manner, the continuous glucose monitor 28 can be used to obtain time-resolved data. Such time-resolved data can be useful to identify fluctuations and trends that would otherwise go unnoticed with spot monitoring of blood glucose levels and standard HbA1c (glycated haemoglobin) tests. Such as, for example, low overnight glucose levels, high blood glucose levels between meals, and early morning spikes in blood glucose levels as well as how diet and physical activity affect blood glucose along with the effect of therapy changes.

In addition to collection device 24, clinicians 14 can prescribe other diabetes therapy devices for patients 12 such as an ambulatory insulin pump 46 as well as electronically based insulin pen 48 (FIG. 1). The insulin pump 46 can record and provide insulin dosage and other information, as well as the electronically based insulin pen 48, to a computer, and thus can be used as another means for providing glucose monitoring data.

It is to be appreciated that embodiments of the computer-implemented method described hereinafter can be implemented electronically on system 41 (FIG. 2), patient computer 18, clinician computer 25, collection device 24 or on any electronic device/computer that includes a display. Specifically, when the computer-implemented method is executed as a program, i.e., software 34, instructions codes of the program can be executed by one or more processors (e.g., processor 76, processor 102, graphics processor 80, and/or display interface 106) to perform the processes associated therewith. In still other embodiments, some or all of the processes of the software 34 discussed hereafter provided on a non-transient computer readable medium 40 storing program instruction codes that, when executed by one or more processors, causes at least a display communicatively coupled to the one or more processors to perform the processes associated therewith.

Figure 4:
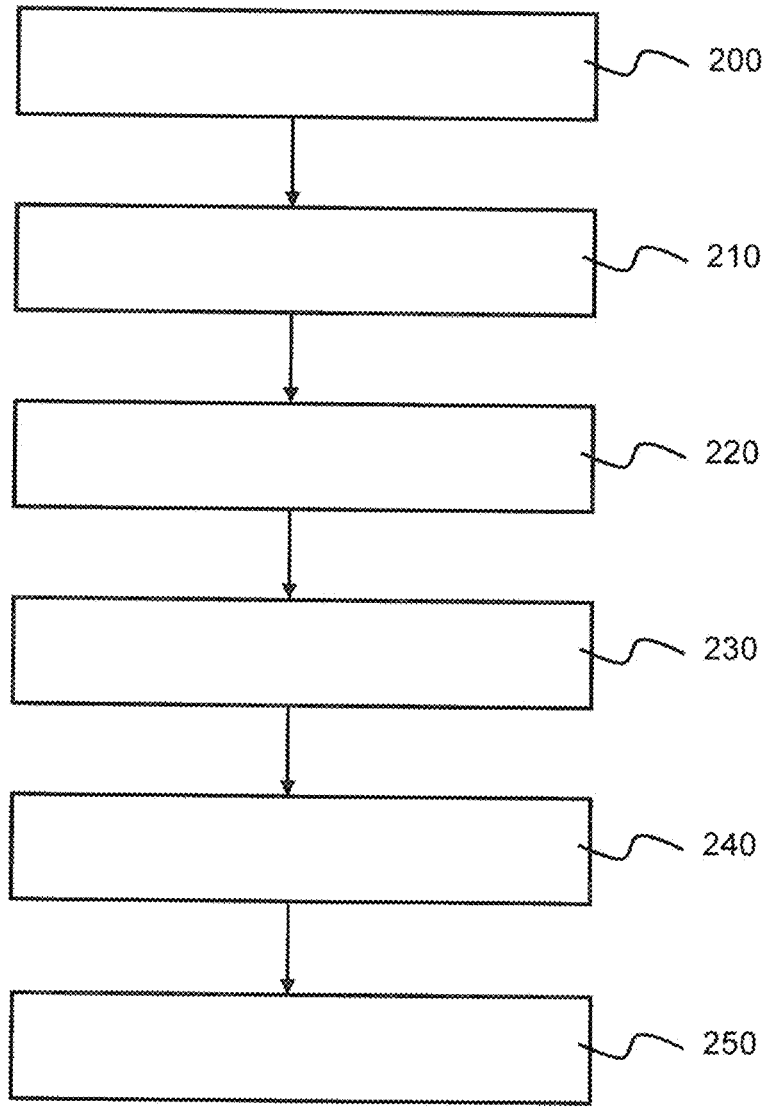
FIG. 4 is a schematic block diagram of a method for analyzing glucose monitoring data indicative of a glucose level.

FIG. 4 shows a schematic representation of a block diagram with regard to a method for analyzing glucose monitoring data indicative of a glucose level. Continuous or discontinuous glucose monitoring data may be analyzed.

In step 200, a graphical window is presented on a display device communicatively coupled to the data processing device, wherein the graphical window comprises a time abscissa axis that defines time units, and a glucose ordinate axis that defines glucose units. The data processing device, for example, may be provided in the data collection device 24 or the patient computer 18. In step 210, glucose monitoring data are received in the data processing device. The glucose monitoring data are indicating a glucose level for a person in a bodily fluid over a monitoring time period in a continuous or discontinuous glucose level measurement.

The plurality of glucose monitoring values is segmented into a plurality of glucose monitoring traces indicative of the glucose level by the data processing device in step 220.

Each of the plurality of glucose monitoring traces spans a time segment of the monitoring time period. The glucose monitoring traces may span over the complete monitoring time period or part of it. In step 230, a reference trace segment is defined by the data processing device. The reference trace segment may define a special trace segment comprising one or more trace points. The reference trace segment refers to a characteristic trace part which potentially is to be found in each of the plurality of glucose monitoring traces. For example, a local maximum, a local minimum and/or an inflection trace point may be defined to be characterizing the reference trace segment.

In step 240, the reference trace segment is determined in each of the plurality of glucose monitoring traces. If the glucose monitoring traces are representing the glucose level in dependence on time, the reference trace segment usually will be present at different sample times for different glucose monitoring traces. For example, a (local) minimum will be assigned to different times along the time abscissa axis for the different glucose monitoring traces. With regard to determining the reference trace segment for each of the glucose monitoring traces, such aspect of time is disregarded. Rather, the reference trace segment is determined by an analysis of the trace or curve as such without referring to the sample time assigned to the trace segment.

The plurality of glucose monitoring traces is plotted within a graphical window on the display device in step 250, wherein the plurality of glucose monitoring traces are aligned to the reference trace segment. Within the graphical window the reference trace segments of the different glucose monitoring traces plotted are overlaying or overlapping each other in the graphical representation due to the alignment.

Figure 5:
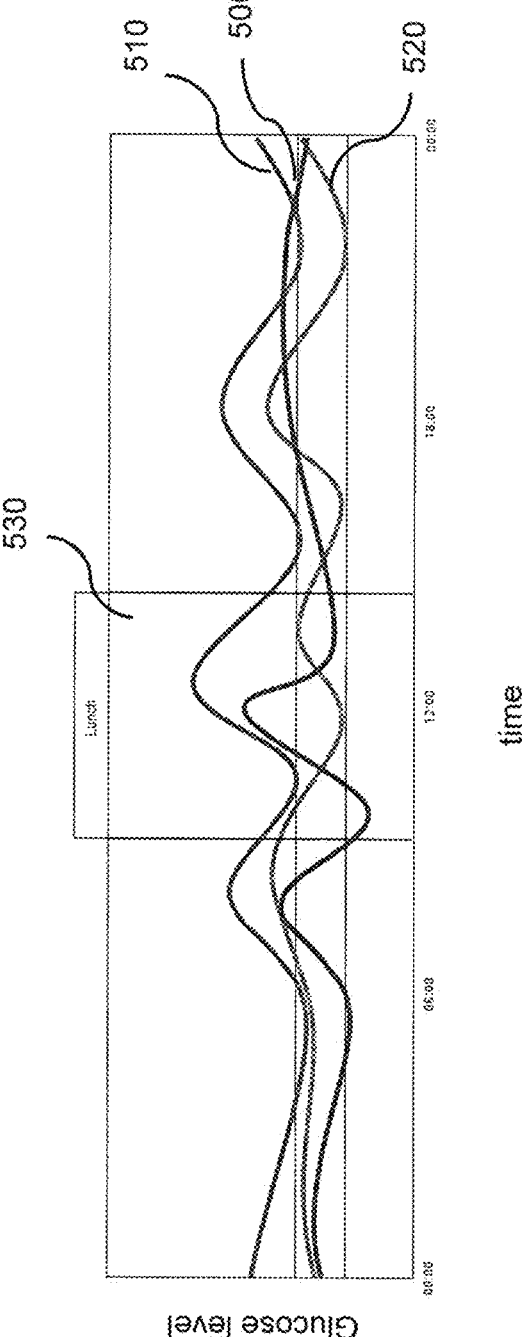
FIG. 5 is a graphical representation of a plurality of continuous glucose monitoring traces.
Figure 6:
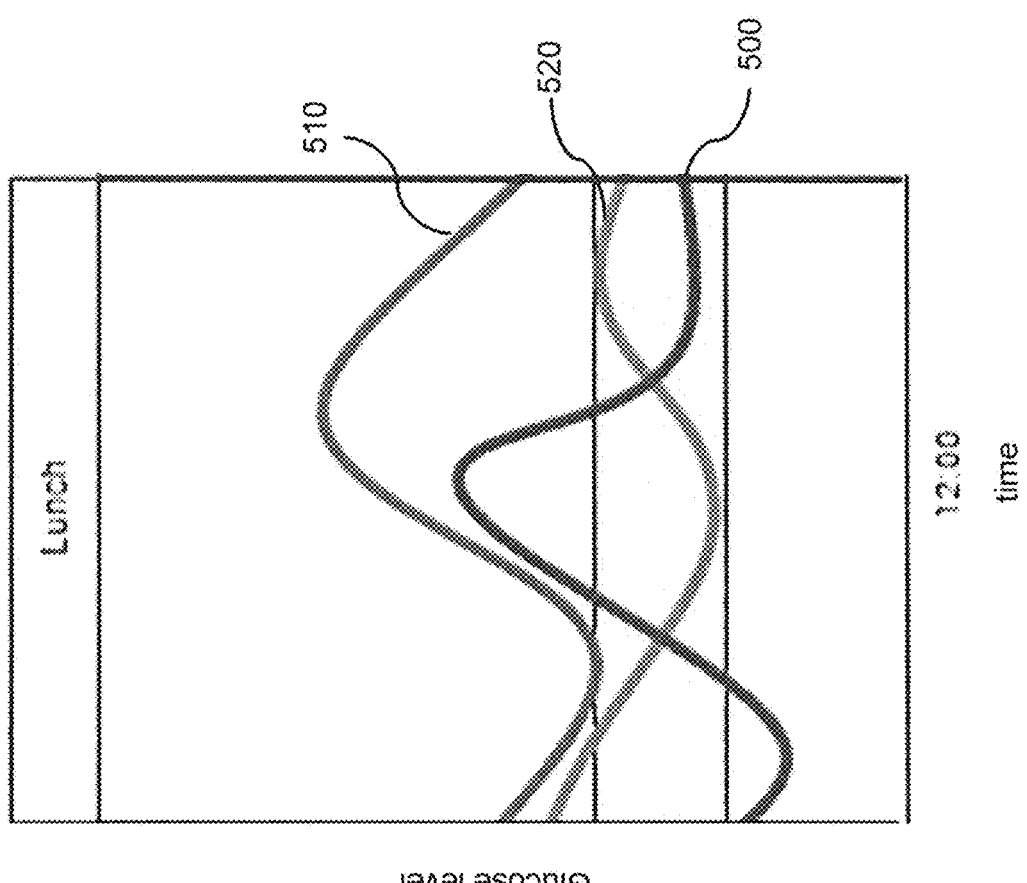
FIG. 6 is a graphical representation of a selected time segment "Lunch" from the schematic representation in FIG. 5.
Figure 7:
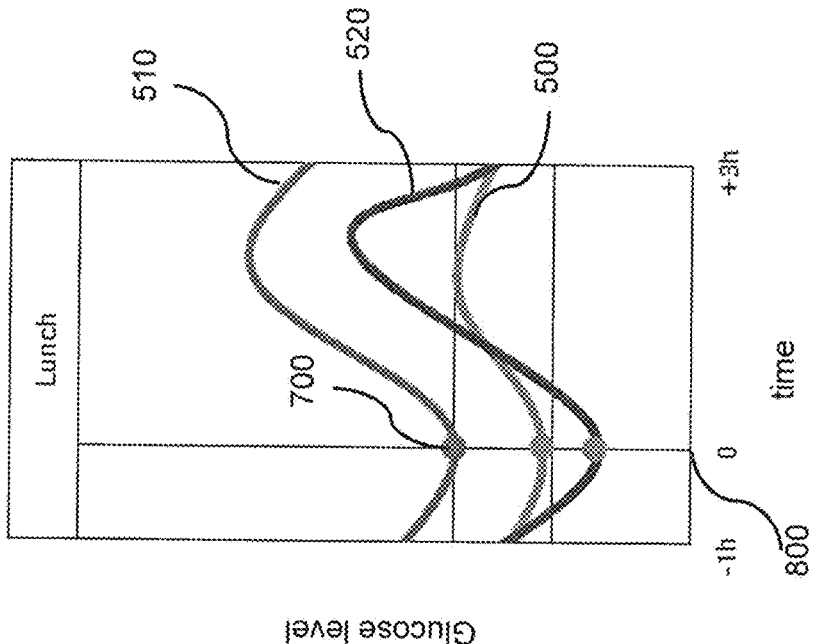
FIG. 7 is a graphical representation of the plurality of the continuous glucose monitoring traces aligned to a reference trace segment which is a local minimum glucose level.

FIGS. 5 to 7 show graphical representations of a plurality of continuous glucose monitoring traces 500, 510, 520. The plurality of continuous glucose monitoring traces 500, 510, 520 represent the monitoring glucose level overtime. The continuous glucose monitoring traces 500, 510, 520 are depicted for a monitoring time of 24 hours. The continuous glucose monitoring traces 500, 510, 520 are scaled according to the time abscissa extending over 24 h.

Referring to FIG. 5, vertical lines define a trace range selection 530 assigned to the event "Lunch". FIG. 6 shows a graphical representation of the plurality of continuous glucose monitoring traces 500, 510, 520 for the time window according to the time abscissa extending from approximately 9:10 to approximately 14.20 (event "Lunch"). The continuous glucose monitoring traces 500, 510, 520 are scaled according to the time abscissa extending from approximately 9:10 to approximately 14:20.

Within such time window for each of the plurality of continuous glucose monitoring traces 500, 510, 520 a minimum value 700 is determined. FIG. 7 shows a graphical representation of a plotting, for the time window comprising the reference trace segment "minimum value", of the plurality of continuous glucose monitoring traces 500, 510, 520, wherein the minimum glucose values 700 are aligned to a reference time 800. In addition, the continuous glucose monitoring traces 500, 510, 520 may be aligned with regard to a reference glucose value (not shown). Such alignment which may be done in addition or as an alternative will lead to "collapsing" of the minimum value 700 for the continuous glucose monitoring traces 500, 510, 520 into a single normalized point, which is, with regard to the glucose ordinate axis, the reference glucose value.

With regard to FIGS. 5 to 7, the continuous glucose monitoring traces 500, 510, 520 are scaled according to the glucose ordinate axis defining glucose level in relative units.

While this invention has been described as having an exemplary design, the present invention may be further modified within the spirit and scope of this disclosure. This application is therefore intended to cover any variations, uses, or adaptations of the invention using its general principles.

What is claimed is:

1. A method for analyzing glucose monitoring data indicative of a glucose level, comprising:

presenting, by a data processing device provided with one or more processors, a graphical window on a display device communicatively coupled to the data processing device, wherein the graphical window comprises a time abscissa axis that defines time units and a glucose ordinate axis that defines glucose units;

receiving a plurality of glucose monitoring values associated with a monitoring time period with the data processing device, the plurality of glucose monitoring values indicating a glucose level sampled from a bodily fluid of a person in a glucose level measurement;

segmenting, with the data processing device, the plurality of glucose monitoring values into a plurality of glucose monitoring traces indicative of the glucose level, wherein each of the plurality of glucose monitoring traces spans a measurement time segment of the monitoring time period;

defining, with the data processing device, a reference trace segment and a characteristic point on the reference trace segment, the reference trace segment being one or more points on the glucose monitoring traces corresponding to a curve characteristic of the glucose monitoring traces and the characteristic point corresponding to an identifiable point on the curve characteristic, wherein defining the reference trace segment comprises selecting, with the data processing device, the reference trace segment from the following group of curve characteristics: a local minimum trace segment indicating a local minimum glucose value segment; a local maximum trace segment indicating a local maximum glucose value segment; an absolute minimum trace segment indicating an absolute minimum glucose value segment; an absolute maximum trace segment indicating an absolute maximum glucose value segment; and an inflection trace point;

designating a trace range within each of the plurality of glucose monitoring traces wherein each of the trace ranges has a duration less than the measurement time segment of the corresponding glucose monitoring trace whereby only a portion of each glucose monitoring trace is within a designated trace range;

determining, with the data processing device, the reference trace segment and the characteristic point for each of the plurality of glucose monitoring traces within the respective designated trace range of each of the plurality of glucose monitoring traces, wherein the step of determining, with the data processing device, the reference trace segment is performed by conducting a search for the reference trace segment without reference to the time abscissa axis or a sample time; and wherein the characteristic points of the plurality of glucose monitoring traces define a plurality of distinct glucose values;

plotting, for a time window comprising the reference trace segment of each of the plurality of glucose monitoring traces, the plurality of glucose monitoring traces within the graphical window, wherein the plurality of glucose monitoring traces are scaled according to the time abscissa axis and the glucose ordinate axis, and the plurality of glucose monitoring traces are aligned with regard to the characteristic point of the reference trace segment of each of the plurality of glucose monitoring traces;

wherein the plotting further comprises defining, with the data processing device, a reference time along the time abscissa axis and aligning the reference trace segment for each of the plurality of glucose monitoring traces to the reference time; and defining, with the data processing device, a reference glucose value along the glucose ordinate axis to the reference trace segment for each of the plurality of glucose monitoring traces and aligning the plurality of glucose monitoring traces to the reference glucose value by normalizing the characteristic points of all of the plurality of glucose monitoring traces such that all of the characteristic points are represented by a single normalized point and the glucose ordinate axis defines the glucose level in relative units; and identifying a trend of glucose levels based upon a review of the plurality of glucose monitoring traces plotted within the graphical window, changing a dosage of insulin based upon the trend of glucose levels, and administering the dosage to the person.

2. The method according to claim 1, wherein the step of receiving a plurality of glucose monitoring values comprises receiving, with the data processing device, a plurality of continuous glucose monitoring values associated with the monitoring time period, the plurality of continuous glucose monitoring values indicating a glucose level sampled from the bodily fluid of the person in a continuous glucose level measurement.

3. The method according to claim 1, wherein the step of receiving a plurality of glucose monitoring values comprises receiving, with the data processing device, a plurality of discontinuous glucose monitoring values associated with the monitoring time period, the plurality of discontinuous glucose monitoring values indicating a glucose level sampled from the bodily fluid of the person in a discontinuous glucose level measurement.

4. The method according to claim 1, wherein the step of designating the trace range comprises determining, with the data processing device, a trace range selection from a selection parameter received by the data processing device.

5. The method according to claim 4, wherein the selection parameter is selected from the following group: day; day of the week; and daytime.

6. The method according to claim 1, wherein the step of defining a reference trace segment comprises defining, by the data processing device, the reference trace segment in response to receiving a user input by the data processing device through an input device communicatively coupled to the data processing device.

7. The method according to claim 1, wherein for at least two of the plurality of glucose monitoring traces the reference trace segment is assigned to a different sample time.

8. The method according to claim 1, further comprising the step of reviewing the effect of the change in dosage by subsequently reviewing time-resolved data from a continuous glucose monitor.

9. The method according to claim 1, wherein the measurement time segment of each of the plurality of glucose monitoring traces spans a 24 hour time period and each of the trace ranges spans a predefined time period having a common start time and a common end time with a duration of less than 24 hours.

10. The method according to claim 1, further comprising the step of generating a data interpretation output to facilitate the management of a physiological condition of the person and which includes trend-monitoring graphs.

11. The method according to claim 10, wherein the data interpretation output is a hard-copy output.

* * * * *